United States Patent [19]

Parziale et al.

[11] 4,267,308

[45] May 12, 1981

[54] LAYERED ZIRCONIUM BIS(BENZENEPHOSPHONATE) INORGANIC POLYMERS

[75] Inventors: Victor E. Parziale, Irvine; Martin B. Dines, Santa Ana; Peter M. DiGiacomo, Mission Viejo, all of Calif.

[73] Assignee: Occidental Research Corporation, Irvine, Calif.

[21] Appl. No.: 109,444

[22] Filed: Jan. 4, 1980

Related U.S. Application Data

[63] Continuation of Ser. No. 7,275, Jan. 29, 1979, abandoned.

[51] Int. Cl.$^3$ .................... C07F 7/00; C08F 130/02
[52] U.S. Cl. ................... 528/395; 260/429.3; 260/429 J; 528/398
[58] Field of Search ........................ 260/429.3

[56] References Cited

U.S. PATENT DOCUMENTS

| | | | |
|---|---|---|---|
| 2,311,306 | 2/1943 | Ritchey | 260/429.5 X |
| 2,346,155 | 4/1944 | Denison et al. | 260/429.3 X |
| 2,512,063 | 6/1950 | Kreidl et al. | 260/429.3 |
| 3,415,781 | 12/1968 | Block | 260/429.5 X |
| 3,426,050 | 2/1969 | Dade | 260/429.3 |
| 3,444,103 | 5/1969 | Maguire | 260/42 R X |
| 3,457,195 | 7/1969 | Block et al. | 260/429.5 X |

OTHER PUBLICATIONS

Alberti et al., J. Inorg. Nucl. Chem. 40, pp. 1113–1117 (1978).
Chemical Abstracts Formula Index 9th, Coll. "$C_6H_7O_3P$" (1972–1976).

Primary Examiner—Helen M. S. Sneed
Attorney, Agent, or Firm—Christie, Parker & Hale

[57] ABSTRACT

Phenylphosphonic acid reacts by a metathesis reaction in a liquid medium with tetravalent zirconium ions, yielding layered crystalline to amorphous inorganic polymers having the empirical formula $Zr(O_3PC_6H_5)_2$. One use for the compound is as a sorbent for small quantities of organic materials in aqueous solutions.

1 Claim, 10 Drawing Figures

LAYERED ZIRCONIUM BIS(BENZENEPHOSPHONATE) INORGANIC POLYMERS

This is a continuation of application Ser. No. 7,725 filed Jan. 29, 1979, now abandoned.

CROSS REFERENCE TO RELATED APPLICATIONS

This application is related to applications Ser. No. 945,971, filed Sept. 26, 1978 and titled "Process for Preparing Layered Organophosphorus Inorganic Polymers," Ser. No. 952,228, filed on Oct. 17, 1978 and titled "Layered Carboxy End Terminated Organophosphorus Inorganic Polymers," and Ser. No. 966,197 filed on Dec. 4, 1978 and titled "Layered Sulfonate End Terminated Organophosphorus Inorganic Polymers," the entire disclosures of which are incorporated herein by this reference.

BACKGROUND OF THE INVENTION

The present invention is directed to solid inorganic polymers having phenyl groups anchored to the surfaces of the polymers. The polymers formed can be layered crystals which display intercalation activity, or they can be partially or totally amorphous.

The interface surfaces of solids are responsive regions of chemical and physical action. Many practical chemical and physical phenomena such as absorption, corrosion, inhibition, heterogeneous catalysis, lubrication, ion exchange activity, adhesion and wetting and electrochemical activity occur on or as a consequence of the presence of a definable solid surface. Solid agents are preferred in most processes over solution or homogeneously dispersed reactive alternatives primarily because they greatly simplify efficient separation of products from reactants. However, solids invariably suffer from deficencies in activity and selectivity in the conversions they effect, due to inherent heterogeneity in the active sites which arises from the nature of their surface structure. Furthermore, much of the active sites are usually buried within the surface, and as a result of these factors, elevated temperature and low conversions are typically required to make a process effective. Exceptions in which homogeneous agents have been used include the Monsanto process for the production of acetic acid from methanol and carbon monoxide employing rhodium, the production of linear alcohols from olefins and syngas, ethylene oxidation by the Wacker process, catalysis of olefins to form polymers, and other polymerization systems.

In an effort to achieve the best features of both homogeneous and heterogeneous processes, efforts have been made to chemically "anchor" known effective solution agents such as phosphines, nitriles, cyclopentadiene and the like, onto certain solids. Porous inorganic surfaces and insoluble organic polymers have been employed. Silica has been the inorganic of choice, the bonded ligand being attached by reaction with the —OH groups projecting from the surface. The organic polymer most used has been polystyrene, with an appropriate metal-coordinating function bonded via the phenyl rings. Results have been generally encouraging. However, there have been pervasive problems deriving from the non-uniform situation of sites which has manifested itself in loss of expected selectivity, activity and even in attrition.

Many inorganic solids crystallize with a layered structure and present sites for anchoring active groups. In this form, sheets or slabs with a thickness of from one to more than seven atomic diameters lie upon one another. With reference to FIG. 1, strong ionic or covalent bonds characterize the intrasheet structure, while relatively weak van der Waals or hydrogen bonding occurs between the interlamellar basal surfaces, in the direction perpendicular to their planes. Some of the better known examples are prototypal graphite, most clay minerals, and many metal halides and sulfides. A useful characteristic of such materials is the tendency to incorporate "guest" species in between the lamella.

In this process, designated "intercalation", the incoming guest molecules, as illustrated in FIG. 2, cleave the layers apart and occupy the region between them. The layers are left virtually intact, since the crystals simply swell in one dimension, i.e., perpendicular to the layers. If the tendency to intercalate is great, then the host layered crystal can be thought of as possessing an internal "super surface" in addition to its apparent surface. In fact, the potential surface is greater than the actual surface by a factor of the number of lamella composing the crystal. This value is typically on the order of $10^2$–$10^4$. Although edge surface is practically insignificant compared to basal surface, it is critical to the rate of intercalation, since the inclusion process always occurs via the edges. This is because bonding within the sheets is strong, and therefore, penetration of the sheets is an unlikely route into the crystal.

Previous studies of the intercalative behavior of layered compounds have mainly been conducted by solid state chemists interested in the bulk effects on the layered host materials. Graphite has, for example, been extensively studied from an electronic point of view. In general, the function of the host is essentially passive. That is, on intercalation the host serves as the matrix or surface with which the incoming guest molecules interact, but throughout the process and on deintercalation the guests undergo only minor perturbation.

In order for a more active process to occur during intercalation, such as selective fixation or catalytic conversion, specific groups must be present which effect such activity. There might also be some preferable geometric environment about each site, as well as some optimal site-to-site spacing. These considerations have not been extensively applied to intercalation chemistry simply because such kinds of active groups required are not found on layered surfaces.

A approach in which catalytically active agents have been intercalated into graphite or clays for subsequent conversions has been described in "Advanced Materials in Catalysis," Boersma, Academic Press, N.Y. (1977), Burton et al, editors, and "Catalysis in Organic Chemistry," Pinnavia, Academic Press, N.Y. (1977), G. V. Smith, editor, each incorporated herein by reference. In neither case could it be shown that any activity was occurring within the bulk of solid. Rather, it is believed that edge sites are responsible for the reactivity observed. In none of the cases was the active site covalently anchored, or fixed upon the lamella of the host. Instead, the normal ionic or van der Waals forces of intercalated guests were operating.

One of the few layered compounds which have available sites is zirconium phosphate $Zr(O_3POH)_2$. It exists in both amorphous and crystalline forms which are known to be layered. In the layered structure, the site-site placement on the internal surfaces is about 5.3 Å, which leads to an estimated 25 Å² area per site. This area can accommodate most of the functional groups desired to be attached to each site. The accepted structure, symbolized projection of a portion of a layer of this inorganic polymer and a representation of an edge view of two layers, are shown respectively in FIGS. 3, 4 and 5.

Besides the advantageous structural features of zirconium phosphate, the material is chemically and thermally stable, and non-toxic.

Quite a bit of work has been conducted on the zirconium phosphate, mainly because it has been found to be a promising inorganic cation exchanger for alkali, ammonium and actinide ions, see Alberti, "Accounts of Chemical Res." 11, 163, 1978, incorporated herein by reference. In addition, some limited work has been described on the reversible intercalation behavior of layered zirconium phosphate toward alcohols, acetone, dimethylformamide and amines, Yamaka and Koizuma, "Clay and Clay Minerals" 23, 477 (1975) and Michel and Weiss, "Z. Natur," 20, 1307 (1965) both incorporated herein by reference. A. Yamaka described the reaction of this solid with ethylene oxide, which does not simply incorporate between the layers as do the other organics, but rather was found to irreversibly react with the acidic hydroxyls to form a covalent bonded product, Yamaka, "Inorg. Chem." 15, 2811, (1976). This product is composed of a bilayer of anchored ethanolic groups aimed into interlayers. The initial layer-layer repeat distance is expanded from about 7.5 Å to 15 Å, consistent with the double layer of organics present. The overall consequence of this reaction is to convert inorganic acid hydroxyls to bound organic alkanol groups. This conversion, while of interest, has limited if any improvement over the hydroxyls already available on zirconium phosphate.

A very recently reported effort in the field is Alberti, et al., "J. Inorg. Nucl. Chem.," 40, 1113 (1978) which is incorporated herein by reference. A method similar to that of this invention for the preparation of zirconium bis(benzenephosphonate), zirconium bis(hydroxymethanephosphonate)monohydrate, and zirconium bis(monoethylphosphate) is described, with descriptions of the properties for these products.

SUMMARY OF INVENTION

According to the present invention there is provided inorganic polymers having phenyl groups pendant to phosphorus atoms wherein the phosphorus atoms are, in turn, linked by oxygen to tetravalent zirconium atoms. The pendant phenyl groups are coupled to phosphorus directly.

Compounds provided in accordance with the invention are inorganic polymers providing pendant phenyl groups and which include units of the formula:

$(O_3P-C_6H_5)^{-2}$ in which the phosphorus is structurally linked through each of the available oxygens to zirconium, and wherein the molar ratio of phosphorus to tetravalent zirconium in said inorganic polymer is about 2 to 1.

Phenyl homopolymers which are inorganic phosphonate polymers have the empirical formula:

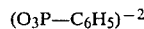

$Zr(O_3PC_6H_5)_2$

The compounds of the invention are formed by a liquid media reaction in which phenylphosphonic acid with the formula:

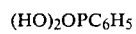

$(HO)_2OPC_6H_5$ is reacted with zirconium ions. The molar ratio of phosphorus to the zirconium in the product is 2 to 1. Reaction, however, preferably occurs in the presence of an excess of phenylphosphonic acid to consume all of the zirconium ions and the zirconium ion is provided as a compound soluble in the liquid media.

The products formed are layered crystalline to semicrystalline to amorphous in nature. They serve as sorbants for organic compounds present in small amounts in aqueous solutions.

Multicomponent polymers, containing other organic groups interspersed with the phenyl group, can be prepared.

THE DRAWINGS

Figure 1:
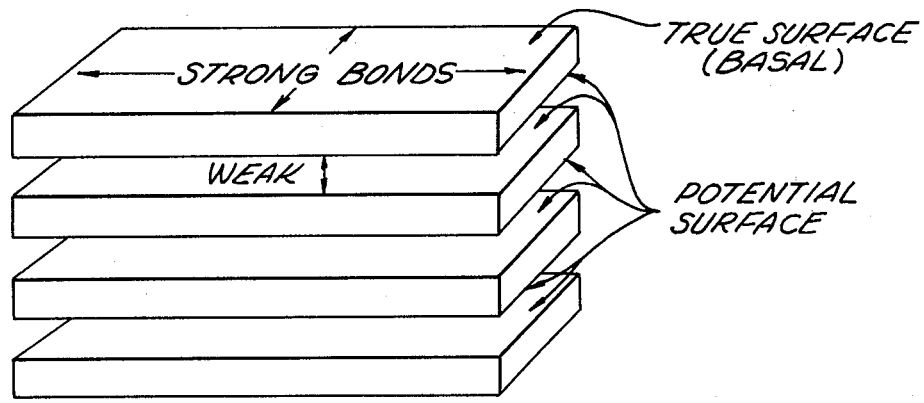
FIG. 1 illustrates a layered microcrystal. Each lamellar slab is formed of strong covalent bonds and has a thickness of about 10 atoms.
Figure 2:
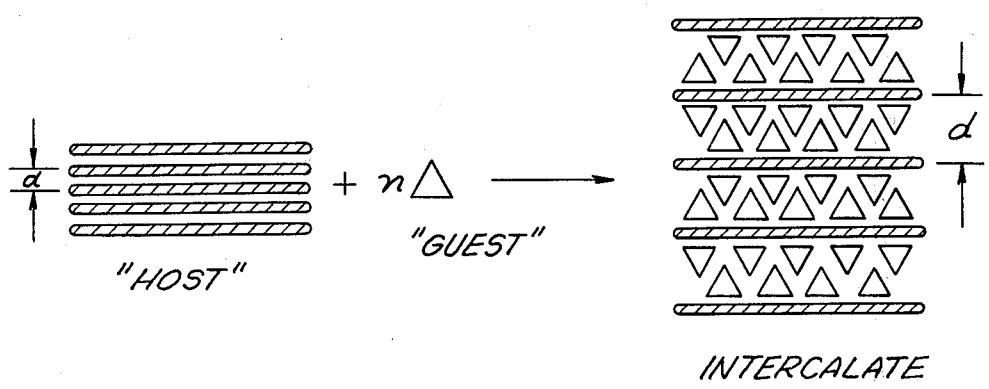
FIG. 2 illustrates intercalation where the interlayer distance is shown as "d."
Figure 3:
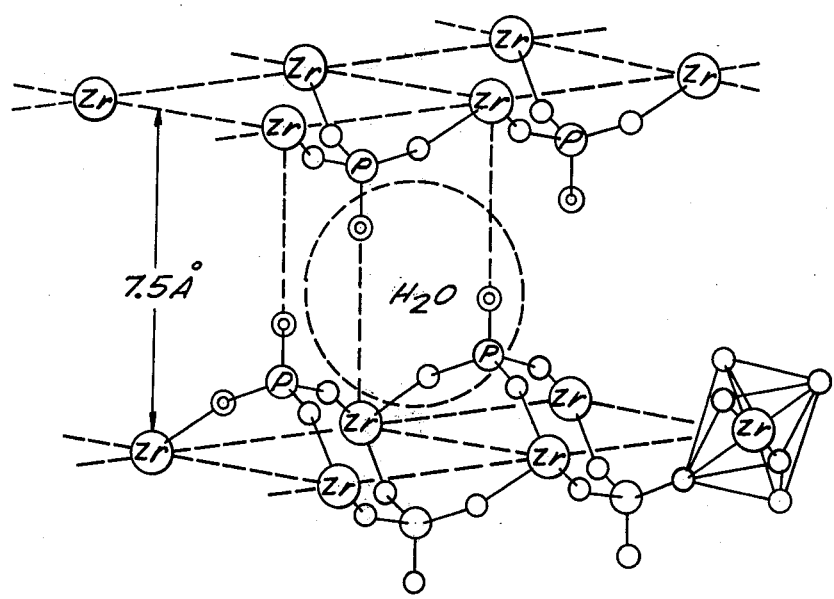

FIG. 3 illustrates the accepted structure for zirconium phosphate and spacing between layers. The dashed lines between zirconium (Zr) atoms is to establish the plane between them. In the drawing P=Phosphorus, O=Oxygen and water of hydration as shown.

Figure 4:
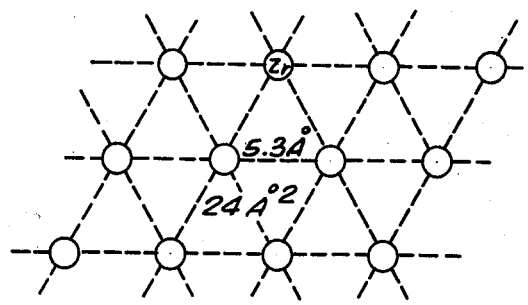

FIG. 4 illustrates a projection of zirconium plane showing accepted spacing between Zr atoms and the available linkage area.

Figure 5:
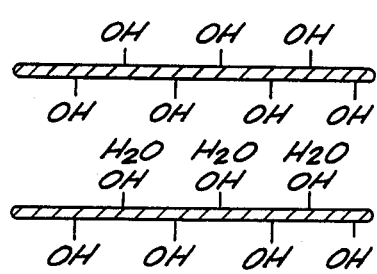

FIG. 5 is a symbolized depiction of spaced zirconium phosphate layers showing covalently bonded hydroxyl groups and water of hydration.

Figure 6:
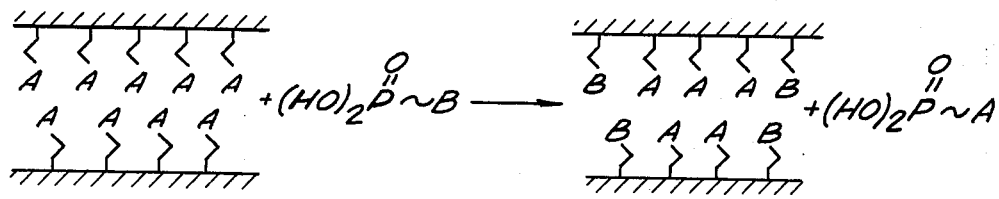

FIG. 6 illustrates an exchange reaction where anchored phenyl groups ("A") are to be substituted by "B," and represents the portion of the organo group linking the terminal group "A" or "B" to the crystals or the organophosphorus acid compound reactant.

Figure 7:
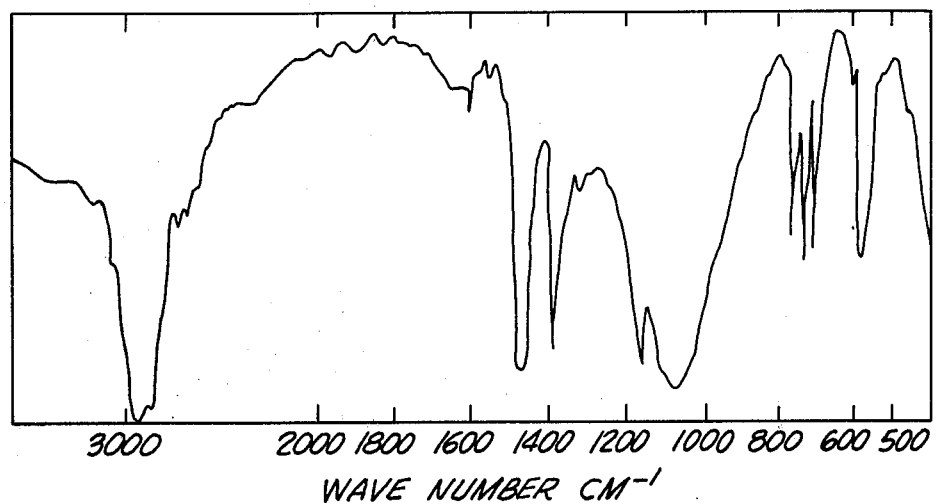

FIG. 7 is an infrared absorption spectrum of the compound prepared in Example 1.

Figure 8:
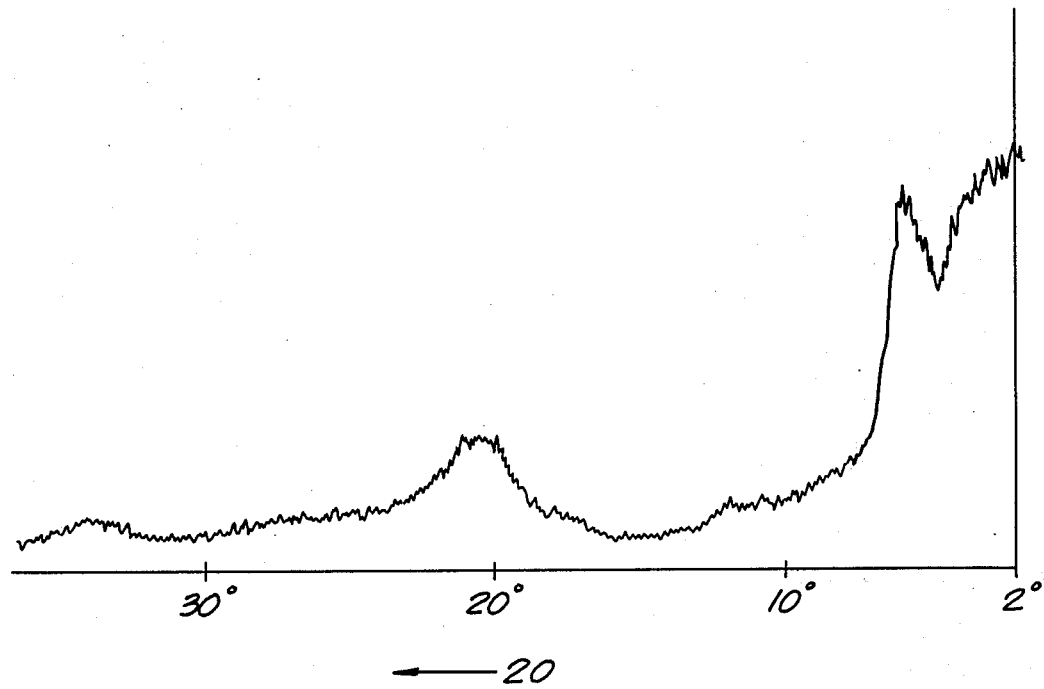

FIG. 8 is the X-ray diffractometer pattern of the compound prepared in Example 2.

Figure 9:
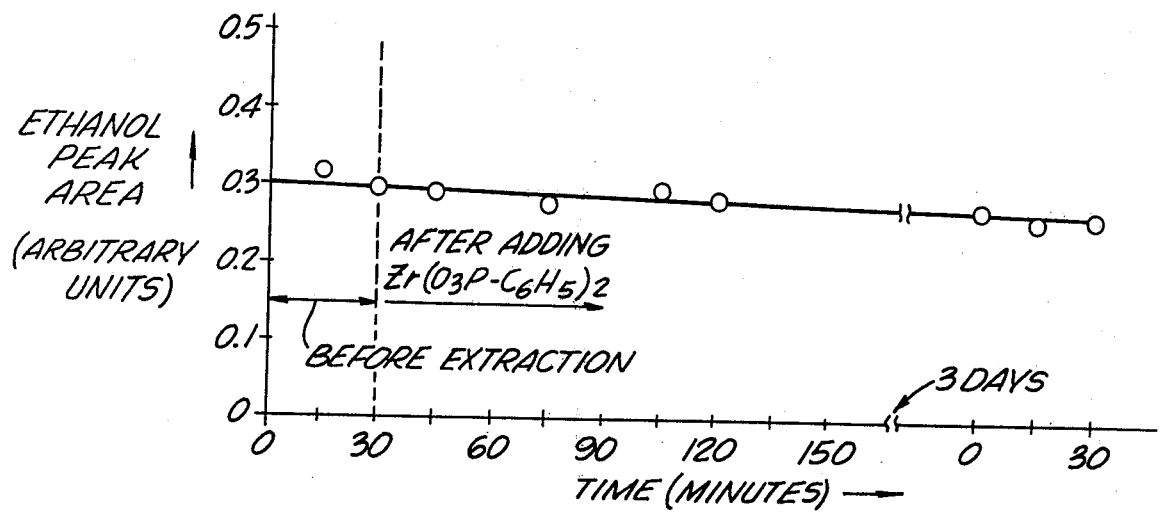

FIG. 9 is a graphical depiction of the ethanol sorption results from the experiment of Example 4.

Figure 10:
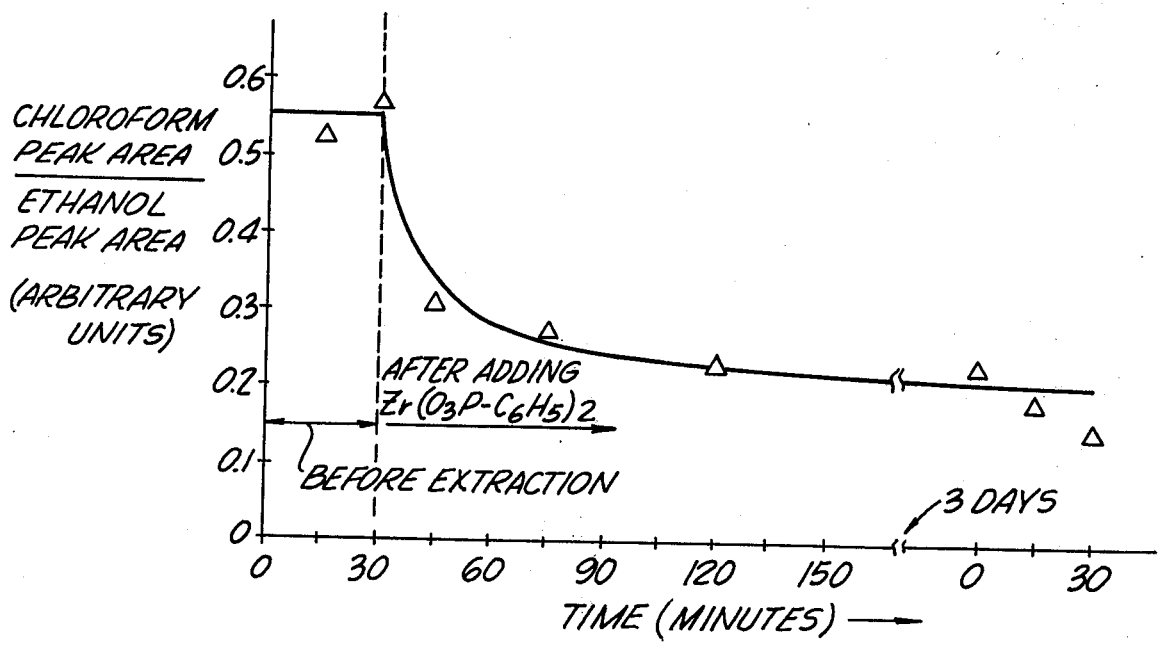

FIG. 10 is a graphical depiction of the chloroform sorption results from the experiment of Example 4.

DETAILED DESCRIPTION

According to the present invention, there is provided crystalline to amorphous inorganic polymers formed of structural units of the formula:

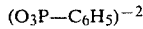

$(O_3P-C_6H_5)^{-2}$ wherein each phosphorus is linked through oxygen to a tetravalent zirconium, and wherein the molar ratio of phosphorus to tetravalent metal in said inorganic polymer is about 2 to 1.

Homopolymers are where inorganic phosphonate polymers have the empirical formula:

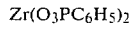

$Zr(O_3PC_6H_5)_2$

The polymers are prepared by a liquid phase metathesis reaction of a phenylphosphonic acid compound having the formula:

with tetravalent zirconium to form a solid inorganic polymer precipitate in which phosphorus is linked to the metal by oxygen and the phenyl group is covalently bonded to the phosphorus atoms. The phenyl group is pendent from the inorganic polymer. Typically, the tetravalent zirconium ion is provided as a soluble salt ZrX wherein X is the anion(s) of the salt. Typical anions include halides such as $Cl^-$, $HSO_4^{-1}$, $SO_4^{-2}$, $O_2C-CH_3^{-1}$, $NO_3^{-1}$, $O^{-2}$ and the like.

The polymeric reaction products formed have been found to be layered crystalline or semi-crystalline in nature and, as such, provide layered structures similar to zirconium phosphate. The amorphous portion of polymers possesses a large quantity of available pendent groups and is similar to silica gel.

The process for the formation of the novel inorganic polymers is a methathesis reaction conducted in the presence of a liquid medium receptive to the tetravalent metal ion at a temperature up to the boiling point of the liquid medium, preferably from ambient to about 150° C. and, more preferably, to about 100° C. at the pressure employed.

While water is the preferred liquid medium, as the phenylphosphonic acid compound is water soluble, an organic solvent such as ethanol or tetrahydrofuran may be employed. There need only to be provided a solvent for the phenylphosphonic acid since the zirconium ion can be dispersed as a solid in the solvent for slow release of the metal ion for reaction with the phenylphosphonic acid.

For complete consumption of the zirconium ions, the amount of acid employed should be sufficient to provide two moles of phosphorus per mole of zirconium. Phosphorous acid and/or phosphoric acid, if present, will enter into the reaction and provide an inorganic polymer diluted in respect to the phenyl groups in proportion to the amount of phosphorous or phosphoric acid employed.

Reaction is virtually instantaneous at all temperatures leading to precipitation of layered crystalline and semi-crystalline inorganic polymer solids.

An amorphous phase may appear as a gel similar to silica gel. The gel can be crystallized by extended reflux in the reaction medium, usually from about 5 to 15 hours. The semi-crystalline product is characterized by a rather broad x-ray powder pattern.

The presence of sequestering agents for the metal ion slows down the reaction and also leads to more highly crystalline products. For instance, hydrogen fluoride is a sequestering agent for zirconium and nitrate ion a sequestering agent for thorium. Both slow the reaction and promote the formation of highly crystalline end products.

As compared to zirconium phosphate forming crystals of 1-5 microns, crystals of 100 to 1000 microns in size have been prepared.

The process of preparation permits a wide variety of inorganic polymers to be formed having the characteristics of the organo group protected by the inorganic polymer structure and with subsequent exchange or substitution reactions, the formation of other inorganic polymers. Polymers formed may be block, random and the like.

A property which adds to the usefulness of the compound is its thermal stability. Thermal characterization may be made by the use of thermal gravimetric/differential thermal analysis. These techniques indicate changes in weight and heat flow of substances as a function of temperature. Thus, decomposition and phase changes can be monitored as temperature increases.

Zirconium phosphate itself is quite a stable material. Interlayer water is lost at about 100° C. and a second dehydration involving the phosphates occurs above 400° C.

The inorganic polymer of this invention is also stabilized toward thermal decomposition as compared to pure organic analogs, as a result of the fixation and separating effect of the inorganic support. Zirconium bis(benzenephosphonate) shows very little weight change up to about 400° C.

In addition to proving the suitability of the compound in elevated temperature applications, the thermal analyses affirm covalent bonding to phosphorus, because normal intercalative interactions are reversed within 10°-100° C. above the boiling point of the guest.

The high surface area of the crystalline products makes them useful for sorption of impurities from aqueous and non-aqueous media.

Another utility is as an additive to polymeric compositions. Similar to the high aspect ratio provided by solids such as mica which improve the stress strain properties of the polymers, the powdered inorganic polymer products of the invention can serve the same function and add features. By the presence of reactive end groups on the bonded organo groups, chemical grafting to the polymer network can be achieved to increase composite crystallinity and elevate heat distortion temperature. In addition, the presence of phosphorus induces flame retardant properties, as would bound halogen.

Still other utilities include solid lubricants which behave like mica, graphite and molybdenum disulfide; solid slow release agents where intercalated materials can be slowly leached or released from the internal layers of the crystals; substances displaying electrical, optical, phase or field changes with or without doping and the like.

While nowise limiting, the following Examples are illustrative of the preparation of solid inorganic polymers of this invention and some of their utilities.

In the Examples conducted in the atmosphere no extraordinary precautions were taken concerning oxygen or moisture. Reagents were usually used as received from laboratory chemical suppliers. The products formed are insoluble in normal solvents and do not sublime. However, the combined weight of yield data, elemental analysis, spectroscopy and powder diffraction results confirm the compositions reported with good reliability.

X-ray powder patterns were run on a Phillips diffractometer using CuK radiation.

EXAMPLE 1

A solution of 2.990 g of $ZrOCl_2 \cdot 8H_2O$ dissolved in 20 ml of deionized water was placed in a round bottom flask fitted with a reflux condenser, stirrer and heating mantle. To this was added 30 ml of an aqueous solution containing 6.040 g of phenylphosphonic acid, with stirring. A white precipitate formed very rapidly. The mixture was heated to about 90° C. and maintained at this level for two days.

After cooling to room temperature, the solid was isolated by filtration, washed with water, washed with acetone, and dried at 55° C. for one hour. The yield was 4.782 g.

The infrared absorption spectrum of this solid is shown in FIG. 7, indicating the presence of an aromatic substituent in the compound. An X-ray diffraction pattern confirmed the expected interlayer spacing of 14.9 Å. Analysis of the solid gave the following results:

| Constituent | Calculated % | Observed % |
| --- | --- | --- |
| Carbon | 35.7 | 37.2 |
| Hydrogen | 2.48 | 3.07 |

These data confirm the empirical formula for the product of $Zr(O_3PC_6H_5)_2$.

EXAMPLE 2

Using the procedure of Example 1, 1.959 g of $ZrOCl_2.8H_2O$ in 150 ml of deionized water was reacted with 1.999 g of phenylphosphonic acid and 1 ml of 38% by weight hydrochloric acid. A white precipitate formed very rapidly. The temperature was raised to afford a gentle reflux, which was maintained for 18 hours, followed by cooling to room temperature.

The solid was isolated by filtration, washed with water and dired at 75° C. for one hour, giving a product weight of 2.56 g which is approximately 100% of the theoretical yield.

The X-ray diffraction pattern of this product is shown as FIG. 8, with an interlayer spacing of 15.2 Å.

EXAMPLE 3

Samples of the product from Example 2 were analyzed by two laboratories for surface area, using a standard BET interpretation of nitrogen coverage obtained both with a dynamic flow method (Quantachrome) and a vacuum static system (Micromeritics). The results were as follows:

| Laboratory | Specific Surface Area ($m^2/g$) |
| --- | --- |
| Micromeritics Corp. | 220 |
| Quantachrome Corp. | 186 |

These values correspond to approximately 50% coverage of the total external and internal (interlamellar) surfaces; the theoretical surface area is about 360 $m^2/g$.

EXAMPLE 4

An aqueous solution of organic compounds for use in sorption experiments was prepared by shaking 25 ml of chloroform, 25 ml of toluene and 25 ml of hexane in a separatory funnel with 100 ml of deionized water for ten minutes. After settling for five minutes, the aqueous layer was separated and stored in a stoppered flask.

A gas chromatographic analysis of the aqueous solution yielded peaks for ethanol (a stabilizer present in the chloroform reagent used), chloroform and water. The ratio of chloroform peak area to ethanol peak area was determined for two samples at 15 minute intervals prior to beginning the sorption experiment.

A 3.060 g portion of the product from Example 1 was added to the aqueous solution, the stopper replaced, and the mixture agitated briefly. After 15 minutes, a sample was withdrawn for gas chromatographic analysis. The mixture was agitated, then allowed to settle for about five minutes prior to obtaining each of the remaining samples in the experiment, the results of which are shown in FIGS. 9 and 10.

Referring to FIG. 9, it can be seen that ethanol was not extracted from the solution in a significant amount. FIG. 10, however, shows that a large amount of the chloroform was extracted by the $Zr(O_3PC_6H_5)_2$ compound. This indicates the utility as a selective sorbent which removes specific contaminants from solutions, while leaving other dissolved materials in solution.

What is claimed is:

1. Layered inorganic homopolymers of zirconium bis(benzene-phosphonate).

* * * * *

UNITED STATES PATENT AND TRADEMARK OFFICE
Certificate

Patent No. 4,267,308                                           Patented May 12, 1981

Victor E. Parziale, Martin B. Dines & Peter M. Di Giacomo

Application having been made by Victor E. Parziale, Martin B. Dines and Peter M. Di Giacomo, the inventors named in the patent above identified, and Occidental Research Corp., the assignee, for the issuance of a certificate under the provisions of Title 35, Section 256, of the United States Code, deleting the name of Victor E. Parziale as a joint inventor, and a showing and proof of facts satisfying the requirements of the said section having been submitted, it is this 27th day of July 1982, certified that the name of the said Victor E. Parziale is hereby deleted from the said patent as a joint inventor with the said Martin B. Dines and Peter M. Di Giacomo.

Fred W. Sherling
*Associate Solicitor.*